United States Patent [19]
Budd et al.

[11] Patent Number: 5,192,313
[45] Date of Patent: Mar. 9, 1993

[54] HEART VALVE PROSTHESIS WITH IMPROVED BI-LEAFLET PIVOT DESIGN

[75] Inventors: John C. Budd; Louis A. Campbell, both of Austin, Tex.

[73] Assignee: Carbomedics, Inc., Austin, Tex.

[21] Appl. No.: 896,831

[22] Filed: Jun. 11, 1992

Related U.S. Application Data

[63] Continuation-in-part of Ser. No. 427,246, Oct. 25, 1989, Pat. No. 5,147,390.

[51] Int. Cl.⁵ .............................................. A61F 2/24
[52] U.S. Cl. ......................................................... 623/2
[58] Field of Search .................. 623/2; 137/512.1, 527, 137/527.8

[56] References Cited

U.S. PATENT DOCUMENTS

| | | | |
|---|---|---|---|
| 4,254,508 | 3/1981 | Bokros | 3/1.5 |
| 4,272,854 | 3/1981 | Bokros | 3/1.5 |
| 4,326,304 | 4/1982 | Klawitter | 3/1.5 |
| 4,328,592 | 5/1982 | Klawitter | 3/1.5 |
| 4,406,022 | 9/1983 | Roy | 3/1.5 |
| 4,443,894 | 4/1984 | Klawitter | 3/1.5 |
| 4,451,937 | 6/1984 | Klawitter | 3/1.5 |
| 4,888,010 | 12/1989 | Bokros | 623/2 |
| 4,995,881 | 2/1992 | Knoch | 623/2 |
| 5,147,390 | 9/1992 | Campbell | 623/2 |

FOREIGN PATENT DOCUMENTS

| | | |
|---|---|---|
| 0211576 | 2/1987 | European Pat. Off. |
| 0356647 | 3/1990 | European Pat. Off. |

Primary Examiner—David J. Isabella
Assistant Examiner—Elizabeth M. Burke
Attorney, Agent, or Firm—John R. Merkling

[57] ABSTRACT

A bi-leaflet heart valve having an annular body and a pair of leaflets. The leaflets pivot around improved ears, whose motion is constrained by generally triangular recesses. The triangular recesses have a pivotal vertex in proximity to a centerline of the annular base and on the upstream side of the heart valve. Opposite the pivotal vertex is a slightly concave base. An upstream wall of the recess is convex.

15 Claims, 5 Drawing Sheets

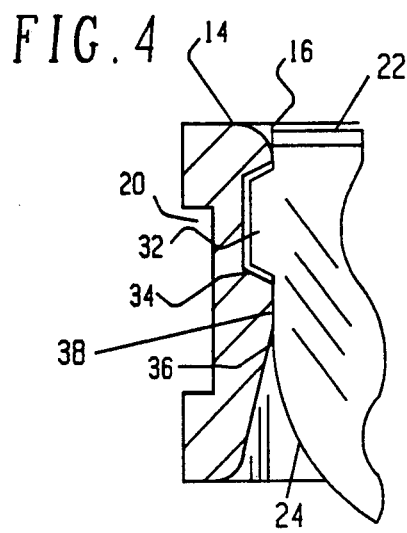
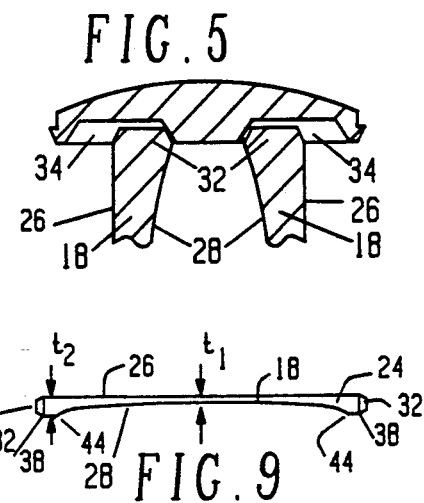
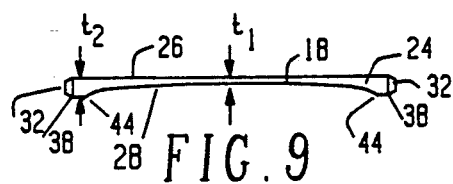
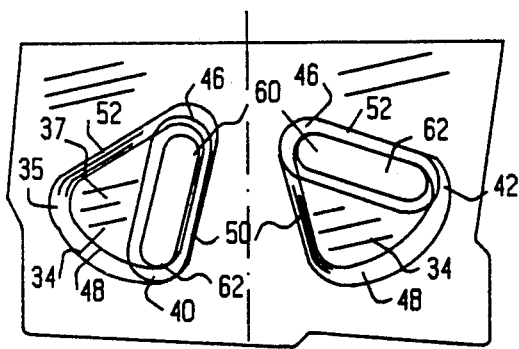
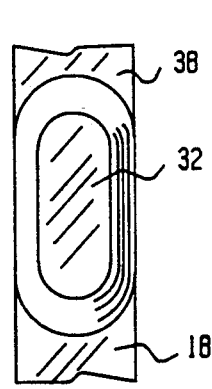
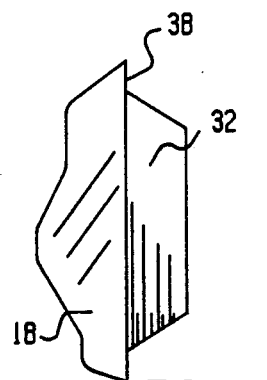

HEART VALVE PROSTHESIS WITH IMPROVED BI-LEAFLET PIVOT DESIGN

This application is a continuation-in-part of co-pending application Ser. No. 07/427,246 filed Oct. 25, 1989, now U.S. Pat. No. 5,147,390.

BACKGROUND OF THE INVENTION

1. Field of the Invention

The present invention pertains to heart valve prostheses and in particular, to bi-leaflet heart valve prostheses using pivotable valve members.

2. Description of Related Art

Various types of heart valve prostheses have been proposed, and many give generally satisfactory operation. One popular design for a heart valve prosthesis includes an annular valve body in which a pair of opposed leaflet occluders are pivotally mounted. The occluders are movable between a closed, mated position, blocking blood flow in an upstream direction, thereby minimizing regurgitation, and an open position, allowing blood flow in downstream direction.

Because hemodynamic energy alone is relied upon for proper operation of the heart valve between its open and closed positions, it is generally desirable to reduce dynamic friction losses in the heart valve which would needlessly burden the cardiac system. Static frictional forces are not significant in a well designed heart valve if there are no surfaces normal to the leaflet's initial opening movement. A complete reversal of the flow direction initiates movement of the occluder away from the surfaces that constrain it from rotation. A certain amount of play in the pivot mechanism is necessary to assure that relatively small and fragile ends of the pivots do not bear the high loads the valve is exposed to when it is fully closed.

Over the countless number of operations of a heart valve, the projections and depressions are subjected to wear. For the reasons set forth in U.S. Pat. No. 4,689,046, to Bokros, also assigned to the Assignee of this Application, spherical projections and depressions are susceptible to significant amounts of "play" in directions lying in the plane of the leaflet and extending generally perpendicular to the diametrical edge thereof. It has been observed that relatively small amounts of wear adjacent the tip of the spherical projection or the corresponding center portion of the recess results in a significant amount of lateral play, even for relatively minute amounts of increased "end play", that is, in directions generally parallel to the diametrical leaflet edge and extending along the hinge points of a leaflet. As a result of this lateral play, the motion and the sequence, especially the synchronous cooperation of the leaflets, becomes less well defined. As a result, performance of the leaflet may become erratic, as is evidenced, for example, by an asynchronous closure of the valve. While prior art heart valves have generally proven to be very reliable, and to have a projected life expectancy exceeding that of the patient, it is desirable to achieve increased margins of safety by providing a prosthesis which substantially exceeds reliability and performance requirements.

Several other improvements to heart valve prostheses are also desired. For example, it is desirable to impart a more rapid closing time to the leaflet occluders so as to reduce regurgitation. However, such quickening of the closing time should not be accompanied by an increase in noise during operation of the prosthesis, for example, as the leaflet occluders seat against the valve body to block regurgitation. Also, any rebounding of the leaflets should be controlled so as to prevent unnecessary wear, and to conserve hemodynamic energy. Any decrease in valve closing time, therefore, should not contribute to rebounding of the leaflets.

In the past, leaflet occluders have occasionally been slightly undersized so as to allow a purging blood flow around them, even when the leaflets are closed. Such flows wash over edge surfaces of the leaflets and the valve body to prevent clotting that might occur at those locations. The hemodynamic energy of a patient, however, should be conserved. Accordingly, the amount of undersizing of the leaflet occluders must be accurately controlled. Such sizing, of course, depends upon the manufacturing tolerances which can be obtained for the selected geometry of the valve body as well as of the leaflet occluders. Since manufacturing costs are directly related to manufacturing tolerances, alternative arrangements for providing a purging flow around the leaflet occluders, particularly at their hinged connections to the valve body, in a manner which conserves hemodynamic energy, are still being sought.

SUMMARY OF THE INVENTION

A heart valve according to the present invention comprises a bi-leaflet heart valve having an annular body and a pair of leaflets. The leaflets pivot around improved ears, whose motion is constrained by generally triangular recesses. The triangular recesses have a pivotal vertex in proximity to a centerline of the annular base and on the upstream side of the heart valve. Opposite the pivotal vertex is a slightly concave base. In addition, a up stream side of each recess is convex. As the leaflets of the heart valve open, distal ends of the ears slide along the bases as the leaflets move from a closed to an open position. Proximal ends of the ears are constrained within the pivotal vertex by the convex side. When the leaflets are open, the centers of the ears contact the convex wall. In prior designs, the distal end of the ears contacted the upstream wall recess when the leaflets are closed. When leaflets of the valve of the present invention close, proximal portions of the ears are driven into the pivotal vertices of the recesses. The leaflets, therefore, are able to rotate around a point close to the pivotal vertices and, consequently, close to the centerline of the heart valve. The leaflets close with little frictional loss and without binding against the walls of the annular base.

The opening angle of the leaflets can be adjusted by varying the inclination of a wall of the triangular recess adjacent the center line. The opening angle should be adjusted, according to the teachings of the present invention, to minimize energy loss for a particular inside diameter of the heart valve. The optimum opening angle can be determined by in vitro testing using an adjustable valve and a pulse duplicator.

It is a principal object of the present invention to provide a bi-leaflet heart valve prosthesis having pivots comprising ears and recesses which are easy to manufacture. A further object of the present invention is to provide pivots which are close to the centerline of the heart valve.

A further object of the present invention is to provide pivots and leaflets which maximize the orifice size by requiring minimal flattened areas on the interior of the annular body.

Another important object of the present invention is to provide a heart valve prosthesis with improved opening and closing rates resulting from an increase in moment about the pivots.

It is also an object of the present invention to provide pivots which have a relatively large contact area and are, consequently, less subject to wear or fracture.

It is an object of the present invention to provide a bi-leaflet heart valve prosthesis with reduced closing time and an improved quiet operation.

It is a further principle of this invention to minimize hemodynamic energy loss by providing the optimum opening angle for each valve size as determined by in vitro testing of sample valves using a pulse duplicator.

A further object of the present invention is to provide a heart valve which includes a pair of leaflets having projections for mounting to an annular valve body and which cooperate with the valve body to reduce the amount of play, particularly lateral play as defined above, despite wear on the rotating mounting components.

Another object of this invention is to provide means for minimizing hemodynamic energy loss by providing an optimum opening angle for sample valves using a pulse duplicator.

It is also an object of the invention to provide a valve design which can be optimized to minimize energy loss without significant re-design of the valve. These and other objects of the invention will be apparent from the following description, in conjunction with the accompanying drawings.

BRIEF DESCRIPTION OF THE DRAWINGS

FIG. 4 is a fragmentary view taken partly in cross-section along the line 4—4 of FIG. 2;

FIG. 5 is a fragmentary cross-sectional view taken along the line 5—5 of mounting FIG. 6 is a fragmentary side elevational view showing the central portion of the valve body of FIGS. 2 and 3 on an enlarged scale;

FIG. 7 is a fragmentary end view of one corner of the leaflet of the preceding FIGURES showing the mounting ear thereof in greater detail;

FIG. 8 is a fragmentary plan view of the leaflet of the preceding FIGURES showing the mounting ear thereof in greater detail;

FIG. 9 is an end elevational view of the leaflet of the preceding FIGURES;

DETAILED DESCRIPTION OF THE PREFERRED EMBODIMENT

Figure 1:
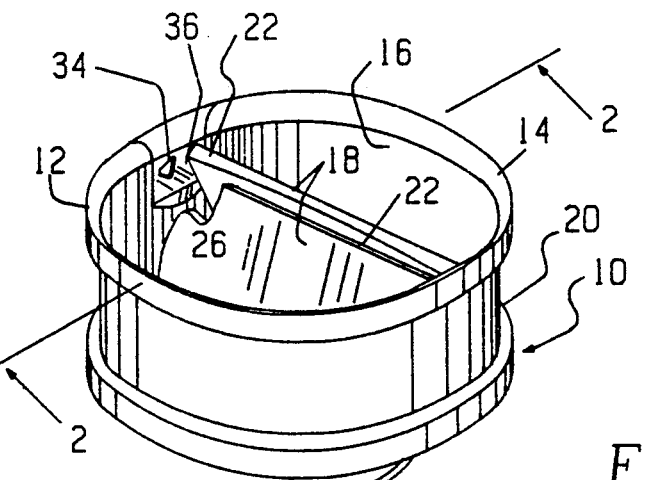
FIG. 1 is a perspective view of a heart valve prosthesis illustrating certain aspects of the present invention, and having one leaflet cut away to disclose a recess.

Referring now to the drawings, a heart valve prosthesis is generally indicated at 10. The prosthesis 10 includes a generally annular valve body 12, having an upper surface 14 and an inner cylindrical surface 16. Disposed within the valve body are a pair of leaflet occluders, or leaflets, generally indicated at 18. The leaflets 18, as will be seen, are mounted for both pivoting and translational movement between open and closed positions.

The outside surface of valve body 12 includes an annular recess or depression 20 for accommodating a suturing ring (not shown) of a conventional type for suturing the heart valve 10 to the heart tissue. As can be seen, the hinge mechanism supporting the leaflet 18 is protected by the valve body against contact with heart tissue or any unraveled sutures which might be present in the immediate area.

The leaflets 18 have an outer edge which extends between upstream and downstream surfaces. The outer edge includes an inner diametrical edge portion 22 which is opposed by an arcuate, and more particularly a semicircular, edge portion 24. According to one aspect of the present invention, the upstream major surfaces 26 of leaflets 18 are generally flat and semicircular in shape. The opposed downstream surface 28 is generally concave in shape, and is preferably part elliptical in configuration, with the focus of the ellipse lying below the leaflet in a mid plane of the leaflet which extends normal to both the leaflet upper surface and the leaflet diametrical edge portion 22. The leaflets 18 are preferably symmetrical about the mid plane thereof. The concave downstream surface 28 is shown in the perspective view of FIG. 1, and is best seen in FIG. 9, which also shows the leaflet symmetry.

Figure 2:
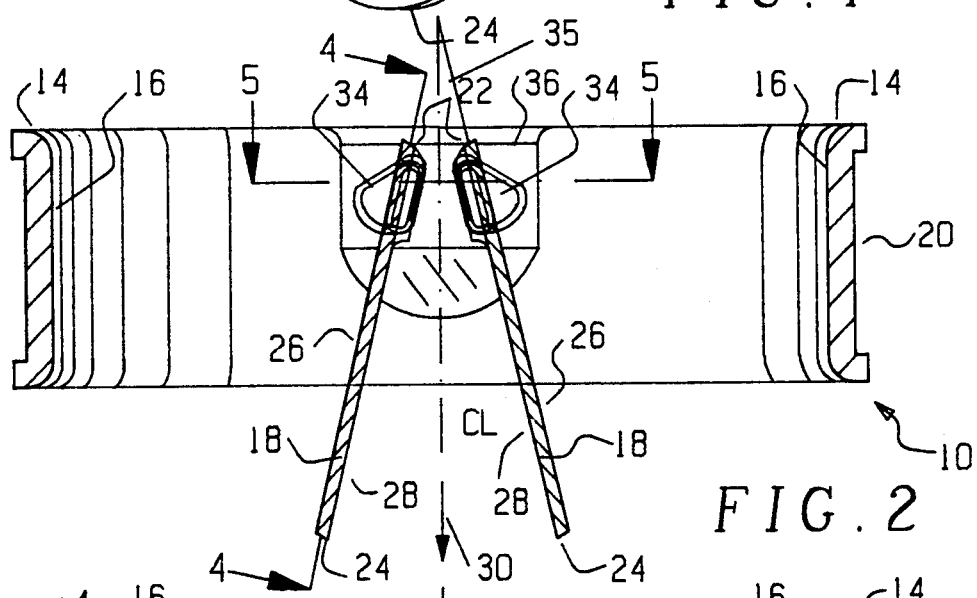
FIG. 2 is a cross-sectional view taken along the line 2—2 of FIG. 1, showing leaflets in an open position.

When in the fully open position of FIG. 2, the leaflets 18 present a minimal impedance to blood flowing in the downstream direction of arrow 30. The concave configuration of downstream leaflet surfaces 28 provides increased clearance for blood flow in a downstream direction, as compared to relatively flat leaflets of thickness comparable to the thickness of the edge portion 24 near mounting ears 32. Having the concave face on the outflow face of the leaflet increases the amount of central flow. Alternatively, the concave surface could be placed on the inflow face if it increases the ease of manufacturing the design without sacrificing the structural or pressure drop advantages achieved with the reduced central thickness.

As mentioned, the leaflets 18 preferably each have a relatively flat upstream face 26 and a concave downstream face. This allows a pivot which is large enough to be easily manufactured. Further, the pivot surface will bear most of the load and most of the wear when the valve is completely open or completely closed. A relatively thick leaflet pivot will be more resistant to structural failure from wear, bending stress or shear stress.

The valve body 12 has been described as having a generally annular configuration with an inner cylindrical surface 16. The cylindrical surface 16 extends throughout most of the valve body interior, except for raised flat surfaces 36 which are generally parallel to one another, extending across chords of the inner cylindrical surfaces 16. The heart valve prosthesis 10 is symmetrical about a valve body mid plane or center line CL, at which edge portions 22 are mated upon valve closing. Recesses 34 are formed in the flat surfaces 36 to provide a hinge mounting for the leaflets 18. Two recesses are required for the mounting of each leaflet, and are located adjacent the diametral edge of that leaflet. Pairs of recesses and leaflets are mirror images about the midplane.

The raised flat surfaces 36 provide surfaces against which the leaflets 18 can pivot. The surfaces 36, however, protrude into the interior of the valve body 12 and, consequently, decrease the flow area available in the valve 10. It is desirable, therefore, to minimize the width of the flat surfaces 36. Placing the recesses 34 close to the mid plane permits the width of the flat surfaces 36 to be minimized, as will be more fully explained below.

The recess 34 forms a generally triangular shaped opening in flat surface 36 with inclined peripheral side walls 35 so that an inner surface is formed identical in shape but smaller than the opening in flat surface 36. The recesses are enlarged with respect to the mounting ears to provide smooth, low friction operation of the leaflet during opening and closing with a considerable portion of the leaflet travel comprising a translational "floating" which is substantially free of frictional engagement with the recess mating edges. FIG. 2 illustrates the preferred location of recesses 34 which maintain the diametrical edges 22 of the leaflet below the upper surface 14 of valve body 12 so as to avoid any contact with heart tissue.

Referring to FIG. 4, the arcuate edge portion 24 of a leaflet is blended into a relatively flat, lateral edge portion 38 adjacent the diametrical edge portion 22. The lateral edge portion 38 provides a relatively close fit with respect to the flat surface 36. According to one aspect of the present invention, the relative size of flat surface 36 is made as small as possible to maximize area available for blood flow through the heart valve prosthesis and to also minimize turbulence in the flow. Outward projections or mounting ears 32 extend from the flat edge portions 38 of a leaflet. The ears 32, extending toward the interior of recess 34, comprise two opposing halves of a truncated cone separated by planer surfaces. Inwardly tapered peripheral walls form a trapezoid in section. As can be seen with further reference to FIGS. 7 and 8, the surface of the mounting ear is trapezoidal in side view and forms a smooth surface of transition.

Figure 3:
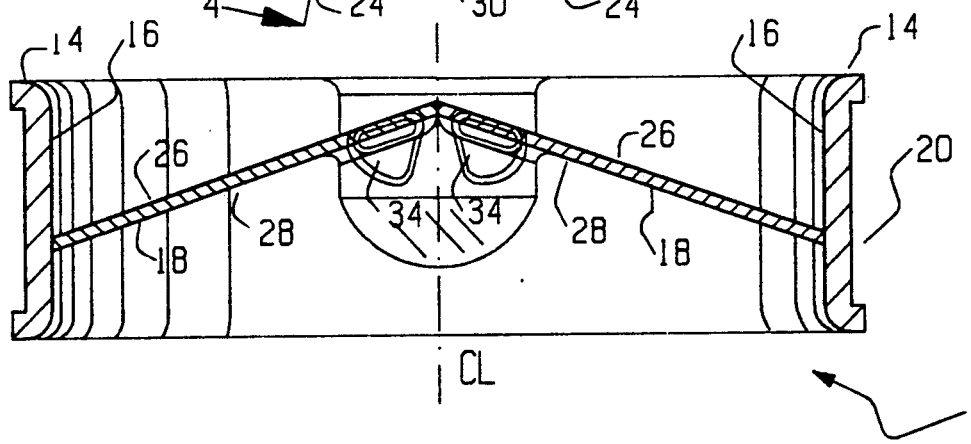
FIG. 3 is a cross-sectional view similar to that of FIG. 2 but showing the leaflets in closed position.

Referring now to FIGS. 2, 3 and 6, the leaflets 18 are moved between open and closed positions in response to blood flow through valve 10. In the open position of FIG. 2 and of the left side of FIG. 6, the mounting ears 32 are seated in a first end portion 40 of recesses 34. As the cardiac cycle continues, blood begins to flow back through the valve 10 into an adjacent upstream chamber of the heart or other upstream blood vessel. The leaflets 18 of the valve 10 close to inhibit back flow. An inner side wall 50 prevents the leaflet 18 from opening completely parallel to centerline CL when the valve 10 is open. The first end portion 40 of the recess 34 is, therefore, further away from the centerline CL than is a pivotal vertex 46 of the recess 34. The pivotal vertex 46 is on the upstream side of the valve 10 when compared to the first end portion 40. As back flow commences, the leaflet 18 moves toward the upstream side of the valve 10 and an upstream ear end 60 moves into contact with the pivotal vertex 46 of the recess 34. The upstream ear end 60 is now in rotational sliding contact with the pivotal vertex 46. Because the ears 18 were inclined away from the centerline, the back flow of the blood imparts a slight torque to the leaflets 18 and the leaflets 18 begin to pivot around the upstream end 60 of the ear 32. Because the upstream end 60 of the ear 32 is relatively close to the diametrical edge 22, the torque acting on the leaflet 18 is maximized and the leaflet 18 tends to close quickly. Moreover, because the upstream end 60 is constrained in the pivotal vertex 46, the path of the semicircular edge 24 is well defined and the leaflet 18 tends to seat against the inner cylindrical surface 16 quickly and accurately.

Figure 10:
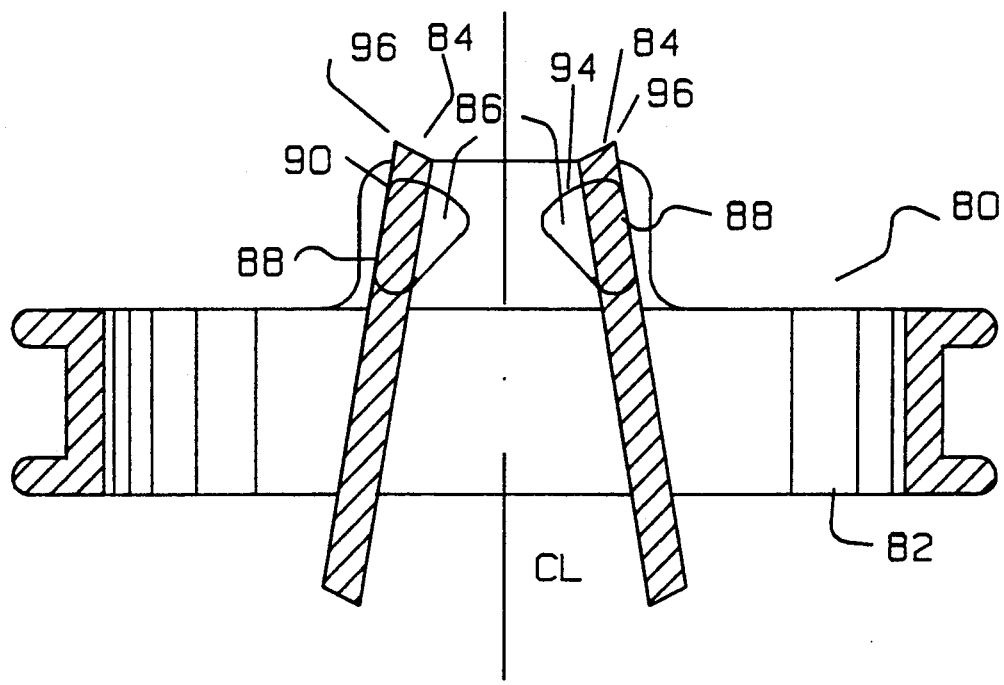
FIG. 10 is a cross-sectional view of a prior art valve.
Figure 11:
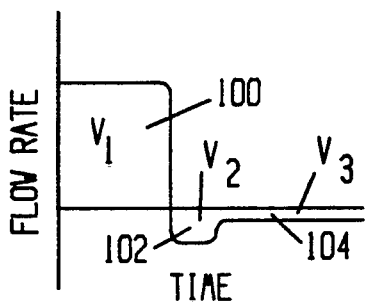
FIG. 11 is a graph of blood flow rate vs. time for a single heart chamber contraction.

This action can be contrasted with the teachings of the prior art as disclosed in U.S. Pat. No. 4,254,508 to Bokros, assigned to the same Assignee as the present Application. A cross-sectional view of a valve, generally designated 80, according to the Bokros patent is shown in FIG. 10. The Bokros valve 80 has an annular body 82 with leaflets 84 which pivot in triangular recesses 86. The orientation of the triangular recesses 86, however, place the leaflets 84 against an outer edge 88 of the recesses 86 when the leaflets 84 are in an open position, as shown in FIG. 10. This displaces the leaflets 84 away from a centerline CL. Three substantially equal areas for the flow of blood through the valve 80 are formed. Because pressure drop energy loss is a function of the effective diameter of an orifice, decreased efficiency can be expected. In Applicant's invention, however, most of the flow passes through two area between the leaflets 18 and the inner cylindrical surface 16 of the valve 10 maximizing the total area through which blood can flow. The opening angle of the leaflets 18 will be on the order of 2 to 8 degrees for a small annular diameter, on the order of 19 mm, and will be 11 to 18 degrees for a large annular diameter, on the order of 29 mm. Small opening angles provide less energy loss from forward flow pressure drop on the smaller diameter valves where pressure drop is the most important component of energy. Likewise, larger opening angle on larger diameter valves provides a reduced closing volume when the forward flow pressure drop energy loss becomes less significant and the closing volume has more effect on the valve's overall efficiency, as more fully explained below.

As the leaflets 84 of the Bokros valve 80 of FIG. 10, begin to close the ear would be in sliding contact with an upstream edge 94 of the recess 86. The path of the leaflet would not be as well defined as that described in this Application. Moreover, the leaflet 84 would be pivoting around an axis further from a diametrical edge 96 of the leaflet 84 which would not only reduce the effective lever arm for closing the leaflet, but would produce a counter torque toward the diametrical edge 96 of the leaflet 84. Also, normal forces between the upper edge 94 and the ears would tend to oppose the closing of the leaflet. These disadvantages are overcome by the configuration described herein.

When the leaflets 18 of the valve 10 are closed as shown in FIG. 3 and in the right half of FIG. 6, the upstream ear end 60 is slightly displaced from the pivotal vertex 46. A downstream ear end 62 is displaced away from a second end 42 in the recess 34. As the pressure of the blood begins to open the leaflet 18, there is no frictional resistance to the movement to the ear 32 at the downstream end 62. The leaflets 18 will begin to pivot. As the leaflets 18 move from their closed position to their open position, the distal ear end 62 will come in contact with a concave side wall 48 of the recess 34. The upstream end 60 of the ear 32 is now in sliding against the inner side wall 50, while the downstream ear end 62 is in generally sliding contact with the concave side wall 48. Normal forces between the downstream ear end 62 and the concave side wall 48 tend to assist the movement of the ear to its open position adjacent inner side wall 50. This contrasts with the action of the Bokros valve 80 where the normal forces between the ear and the leaflet 88 during closing impeded the closing of the valve 80.

Figure 16:
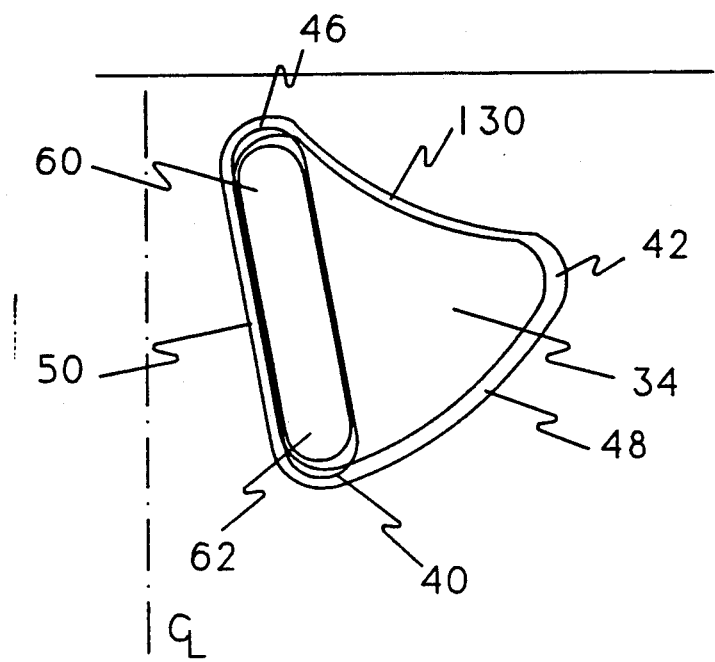
FIG. 16 is a partial view of a pivot having a recess with a convex upstream wall, with lealets open.
Figure 17:
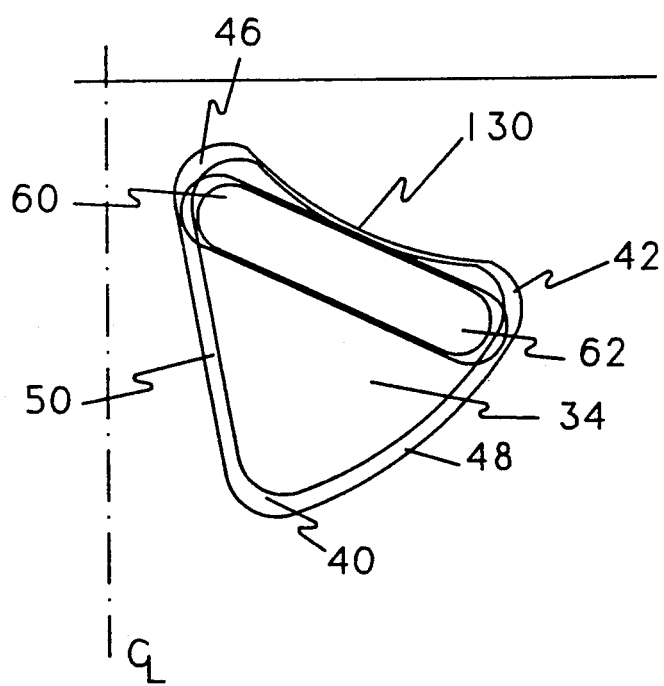
FIG. 17 is a view of the pivot of FIG. 16, with leaflets closed.

An improved recess is illustrated in FIGS. 16 and 17. In addition to the features described above, the improved recesses shown in FIGS. 16 and 17 have a convex upstream wall 130. The convex wall 130 tends to pinch the upstream ear end 60 in the pivotal vertex 46. This implies that the recesses and ears can be manufactured to less exacting tolerances, while still achieving the benefits described heretofore. Moreover, as the leaflets move from open position, shown in FIG. 16, to a closed position shown in FIG. 17, the ears come into contact with the convex wall 130 near the middle of the ear. This implies that the stresses experienced by the ears in the open position will be concentrated toward the centers of the ears instead of at outside ends 60 or 62.

When the leaflets 18 are in their fully open position, the ears 32 press against the inner side walls 50. The leaflet surfaces 28, therefore, are not parallel to flow lines in the blood flow even when the leaflets 18 are in their fully open positions. Each leaflet 18 forms an acute opening angle 35 with the center line CL of the valve 10. This angle 35 is adjusted to minimize hemodynamic energy loss as will now be explained with particular reference to FIGS. 11 through 14.

The loss in cardiac efficiency that is attributable to a heart valve can be divided into three categories. During forward flow a $V_1$ volume 100 of blood must pass through a relatively small valve orifice at a $P_2$ forward pressure 106. The resistance to this flow can be described as $E_1$. When the direction of flow reverses the leaflets begin to close. As the leaflets close a $V_2$ closing volume 102 flows backwards. The $V_2$ volume 102 must be pumped forward again in the subsequent cardiac cycle. There is a $P_2$ pressure impulse 108 associated with the closing of the leaflets 18 and a $P_2$ static back pressure 100 associated with reverse blood flow. The energy required to re-pump the closing volume can be described as $E_2$. A third source of energy loss is the leakage around the leaflets 18 when the valve is closed. This $V_3$ leakage volume 104 can be reduced by a closer fit between the occluders and the orifice without effecting $E_1$ or $E_2$. The value of the energy loss E can be calculated according to the following formula derived from the Bernoulli equation:

$$E = PV = (mv^2)/2$$

Where:
E = Energy loss
P = Pressure difference across the valve
V = Volume
m = Mass of the blood passing through the valve
v = Velocity of blood flow

*In vitro* flow loops have the capability of measuring instantaneous volumetric flow rate Q, as well as differential pressures P while subjecting a valve to pulsatile flow so the energy loss can actually be measured using the equation:

$$E = \int_o^t Q P dt$$

Figure 13:
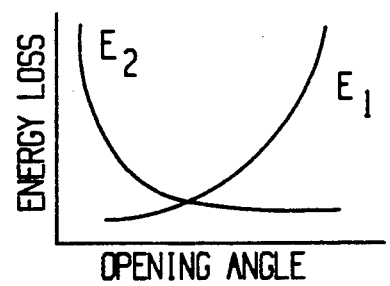
FIG. 13 is a graph of energy loss for forward and backward flow vs. opening angle for a representative valve size.
Figure 12:
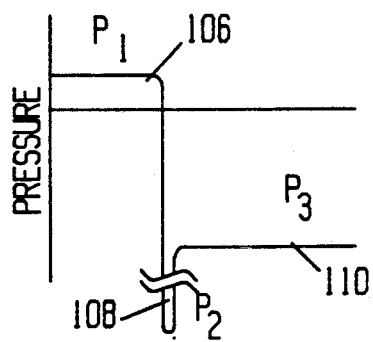
FIG. 12 is a graph of blood pressure vs. time for the contraction.
Figure 14:
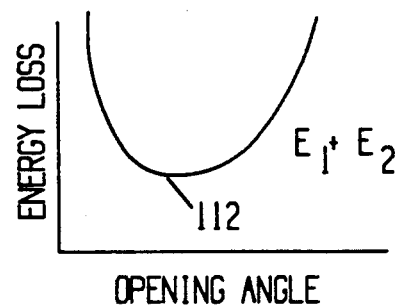
FIG. 14 is a graph of total energy loss vs. opening angle for the valve size.

Using such a flow loop, otherwise identical valves with different leaflet opening angles have been tested. It was determined that the further the leaflets open, the less resistance is seen to forward flow, so a very acute opening angle 35 provides the minimum $E_1$ energy loss as shown in FIG. 13. It was also determined that a very obtuse opening angle 35 minimizes the closing volume and the resultant energy loss $E_2$. A design can therefore be optimized by selecting an opening angle 35 which approaches the minimum 112 of $E_1 + E_2$ as shown in FIG. 14. These empirically derived curves are non-linear. Smaller valves suffer from greater losses of energy from forward flow pressure drop, or $E_1$, and larger valves lose more energy from closing volume, or $E_2$, for any given opening angle 35. The optimum valve would have a very acute opening angle in the small sizes and a much more obtuse opening angle in the larger sizes to provide a minimum valve for $E_1 + E_2$.

The opening angle will be on the order of 1 to 5 degrees for a smallest size, for example from 16 mm to 19 mm total annular diameter, and will increase to 5 to 12 degrees for a large size, for example from 26 mm to 29 mm total annular diameter. A small opening angle provides less energy loss from forward flow pressure drop on the smaller sizes where pressure drop is the most important component of energy. Likewise, a larger opening angles on the larger size valves provides a reduced closing volume when the forward flow pressure drop energy loss becomes less significant and the closing volume has more effect on the valve's overall efficiency.

Figure 15:
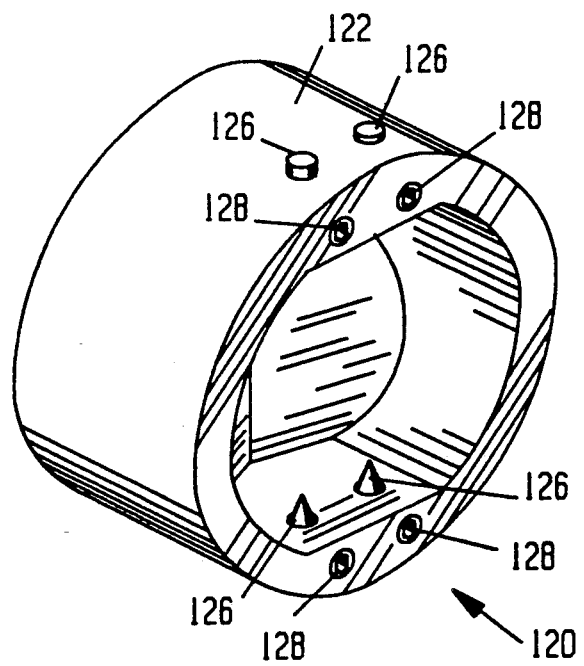
FIG. 15 is a perspective view of an adjustable valve for testing energy loss on a pulse duplicator.

At the present, *in vito* testing for energy optimization has not been achieved. For *in vitro* testing, an adjustable valve 120 as shown in FIG. 15, may be used in a pulse duplicator. The adjustable valve 120 is not intended for implantation and can therefore be constructed of materials which are easily machined but which lack wear resistance and other properties necessary for implantable heart valves. The adjustable valve 120 comprises an annular body 122 with leaflet occluders 124. The leaflet occluders 124 turn on pivots (not shown). For the adjustable valve 120 the pivots are preferably symmetrical, for example, conical or cylindrical, so that the pivots do not restrain the opening angle of the occluders 124. This contrasts with the mounting ears 32 and recesses 34 of preferred embodiments of the invention, as described above. The opening angle is not defined by a feature of the pivot, such as side wall 50, but rather by adjustable conical pins 126. By displacing the pins 126 into or out of the value orifice, the opening angle of the occluders can be adjusted for repeated empirical measurements of pressure and flow, so that information on energy loss for a particular orifice size can be obtained. The pins 126 are secured in a selected position with set screws 128.

Once an optimum angle for a selected orifice size has been determined, the recesses 34 of the invention can be adjusted by changing the position of the side wall 50, without significantly altering the structure of the valve.

The preferred structure of the ears 32 which engage the recesses 34 and of the leaflets 18 now will now be described. Referring to FIG. 9, leaflet 18 is shown in an end elevational view, facing the diametrical edge 22 of the leaflet. The upper, generally flat surface 26 extends between the lateral edges 38 of the leaflet. In the preferred embodiment, the generally part elliptical downstream surface 28 extends nearly the same distance, that is, immediately adjacent the lateral edges 38 of the leaflet, but preferably is extended by relatively flat portions 44. If desired, the flat extensions 44 can be eliminated, as shown in FIG. 5. As can be seen in FIG. 9, the leaflet midplane thickness $t_1$, taken along a central plane of the leaflet, is substantially smaller than the thickness $t_2$ taken at the leaflet lateral edge. The mounting ears 32 have a base at their point of mounting to the leaflet body no larger than the thickness $t_2$ at the lateral edge of the leaflet body so as to avoid any protrusion beyond the upstream or downstream surfaces 26, 28 of the leaflet. The mounting ears 32 are located adjacent the diametrical edge 22 and extend outwardly from the lateral edges 38 in generally opposite directions.

The different curvatures of the upper and lower surfaces of the leaflet conveniently provide regions of increased strength immediately adjacent the mounting ears 32 where the concentration of stress is high, while significantly reducing the mass of the leaflet at the central portion thereof. Leaflet cross-sectional configurations corresponding generally to the shape illustrated in FIG. 9, provide other advantages which improve valve operation. For example, the configuration of the leaflet cross-section provides a leaflet of reduced, minimal mass whose upper surface increases stiffness and prevents disengagement of the leaflet mounting with the valve body. The downstream surface configuration reduces leaflet mass and improves the capture of blood flow with an attendant application of force to the downstream surface of the leaflet, thereby accelerating valve closing and lessening regurgitation. Further, the leaflet cross-sectional configuration conveniently provides lateral edges of localized increased mass immediately adjacent the leaflet mounting ears where stress on the leaflet is the greatest.

Referring now to FIG. 6, recesses 34 include the first and second opposed, generally arcuate end portions 40, 42, respectively and generally arcuate pivotal end portion 46. The first end portion 40 is located spaced from the centerline CL of the prosthesis, the second end portion 42 is located remote from that centerline and above the first end portion 40. The three ends generally form a triangle. The sloping or bevelled, slightly concave side wall 48 extends between the end portions 40, 42. Similar sloping or bevelled but generally linear side walls 50, 52 extend between ends 40 and 46 and 42 and 46, respectively. All of the side walls and ends have an identical slope or bevel with respect of the flat surface 36.

The cross-sectional profile of side wall recesses 34 is generally profiled (see FIGS. 4 and 5) so as to mate with the profile of the mounting ears 32, as illustrated in FIG. 9. As can be seen FIGS. 2 and 3, the recess 34 has an opening greater than the size of the ears 32 so as to allow ear to travel back and forth, toward and away from centerline plane CL as well as upstream and downstream, during leaflet opening and closing. The increased width of the recess provides a clearance which helps to eliminate binding of the ears in their extreme closed and open positions (see FIGS. 2 and 3, respectively).

The tapered configuration of the ears 32 is also preferred because that shape results in less play over the life of the valve prosthesis, particularly as the valve suffers a certain amount of inevitable wear. Even should noticeable wear occur at the end faces of the conical ears, the increase in lateral play of the leaflet (in directions generally normal to the flat upstream surface) has a potential for being much smaller, compared to leaflet ears of other configurations, such as spherical configurations, for example. The potential for reduced wear was explained in U.S. Pat. No. 4,689,046. As pointed out in that patent, small amounts of wear in the outer surface of hemispherical ears results in a more substantial lateral play of the leaflets than is experienced in the preferred frustoconical ears. Depending upon the recess contour and the leaflet configuration and design of its mounting, additional advantages may be realized when conical ears are employed over spherical ears in that, when nested in a similarly contoured recess, the conical ears have a potential for establishing a line contact with the bevelled side walls of the recess, whereas spherical ears, if worn unevenly, tend to establish one or more point contacts with their cooperating, similarly configured recesses.

The mating leaflet ears and cooperating recesses of the preferred embodiment are expected to exhibit a very uniform level of wear over the expected life of a patient fitted with the heart valve 10. This is due in part to the lateral clearance as illustrated in FIG. 4 and the configuration of the recesses which allow the leaflet mounting ears 32 to "float" free of significant frictional contact with the recess side walls as the leaflet is moved between open and closed positions. However, even though the leaflet operates with a relatively low friction, the movement of the leaflets is well controlled throughout the life of valve 10 because of the cooperating ears 32 and complementary-shaped recesses 34 in which the ears ride.

The preferred leaflet configuration, where leaflet thickness is increased at the lateral edges, provides a mounting surface for the mounting ears of increased size, thus insuring that the mounting ears 32 do not protrude beyond the upstream and downstream major leaflet surfaces. This latter feature is particularly important for the preferred part-conical configuration which has an enlarged base portion at its point of joinder with the leaflet edge. As was explained above, the part-conical mounting ears reduce lateral play of the leaflet despite inevitable wear experienced throughout the patient's life.

Several variations in the above-described embodiment are possible. For example, the leaflet mounting ears and the recesses within which they are mounted can be angularly offset corresponding amounts with respect to the leaflet body and valve body, respectively, while preserving the various angular orientations that exist throughout the range of motion of the leaflets within the valve body. In addition, the leaflets 18 can be disposed at any angle to the valve body that may be desired. However, the angular displacement illustrated in FIG. 3 is generally preferred to provide a desired rapid response time in leaflet movement, an efficient utilization of hemodynamic energy to move the leaflets between their open and closed positions, and to help prevent wedging of the leaflets within the valve body when brought to their closed position.

A description of the present forms of the invention having been described by way of example, it is anticipated that further variations of the described forms of the apparatus may be made without departing from the invention and the scope of the appended claims.

What is claimed is:

1. A heart valve prosthesis comprising:

a generally annular valve body configured around an axis and having an inner surface defining a central passageway through which blood flows;

a pair of leaflet occluders proportioned to be pivotally received within said valve body and to move between an open position permitting blood to flow in a downstream direction and a closed position blocking flow of blood in an upstream direction, said leaflet occluders each having a diametral edge;

a generally arcuate edge opposite the diametral edge; and a pair of opposed outwardly protruding mounting ears on the generally arcuate edge adjacent the diametral edge for pivotally mounting the leaflet occluder to the valve body, the mounting ears having a proximal end adjacent the diametral edge; and a distal end spaced away from the diametral edge;

said valve body defining four recesses, a pair for each leaflet occluder, each recess comprising a generally triangular-shaped opening in the valve body inner surface, each said recess further comprising a first arcuate end portion adjacent an upstream side of said annular valve body and configured to periodically receive the proximal end of the respective mounting ear in generally rolling contact and second and third arcuate end portions downstream from said first arcuate end portion with a downstream side wall extending between said first end portion and said second end portion and a convex upstream side wall extending between said first end portion and said third end portion, said second arcuate end portion being adjacent to a center line lying parallel to the axis of the valve body and between the two occluders and said third arcuate end portion being spaced away from said center line, the second end portion being downstream from the third end portion, and said downstream side wall being angled away from the center line from the first arcuate end portion to the second arcuate end portion; and a third side wall extending between said second end portion and said third end portion and configured to periodically receive the distal end of the respective mounting ear in generally sliding contact.

2. A heart valve prosthesis according to claim 1 wherein the third side wall is a concave surface.

3. A heart valve according to claim 2 wherein the mounting ears further comprise radially outwardly tapered walls and each of said side walls of the recesses comprise congruent radially outwardly tapered walls.

4. A heart valve according to claim 3 wherein the recesses each extend to a uniform depth into the valve body.

5. A heart valve according to claim 4 wherein each leaflet occluder further comprises a generally flat upstream surface.

6. A heart valve according to claim 5 wherein each leaflet occluder further comprises a generally concave downstream surface, opposite to the flat upstream surface.

7. A heart valve according to claim 6 wherein the concave downstream surface of the occluders comprises a partial elliptical surface.

8. A heart valve according to claim 7 wherein the partial elliptical surface of the occluders has an axis of revolution below the downstream surface of the leaflet occluder, in a midplane of the occluder which said midplane extends normal to both the flat upstream surface and the diametral edge.

9. The heart valve prosthesis according to claim 1 wherein the arcuate edges of each of the leaflet occluders further comprise a cordial edge perpendicular to the diametral edge at each end of the diametral edge, and wherein one of the mounting ears is located on each cordial edge.

10. The heart valve according to claim 9 wherein the proximal end of the mounting ears comprises a first arcuate segment of a frustro-conical surface and the distal end of the mounting ear comprises a second arcuate segments of a frustro-conical surface, the second arcuate segment being a mirror image of the first arcuate segment, the first and second arcuate segments being spaced away from each other and being joined by inclined surfaces.

11. The heart valve according to claim 10 wherein the first, second and third arcuate end portions of each recess are frustro-conical segments.

12. The heart valve according to claim 1 wherein the downstream side wall is angled away from the center line to the first end portion to the second end portion at an opening angle of from one to eighteen degrees.

13. The heart valve according to claim 2 wherein the downstream sidewall is angled away from the center line from the first end portion to the second end portion at an opening angle of from one to eighteen degrees.

14. The heart valve according to claim 13 wherein the opening angle is about 1 to 5 degrees when a diametrical dimension of the central passageway is from 16 mm to 19 mm.

15. The heart valve according to claim 13 wherein the opening angle is about 5 to 12 degrees when a diametrical dimension of the central passageway is from 26 mm to 29 mm.

* * * * *